US011521752B2

(12) United States Patent
Raman et al.

(10) Patent No.: US 11,521,752 B2
(45) Date of Patent: Dec. 6, 2022

(54) METHODS AND SYSTEMS FOR AUTOMATED SCAN PROTOCOL RECOMMENDATION

(71) Applicant: GE Precision Healthcare LLC, Milwaukee, WI (US)

(72) Inventors: Balaji Raman, Menomonee Falls, WI (US); Bradley Gabrielse, Brookfield, WI (US)

(73) Assignee: GE Precision Healthcare LLC, Milwaukee, WI (US)

( * ) Notice: Subject to any disclaimer, the term of this patent is extended or adjusted under 35 U.S.C. 154(b) by 225 days.

(21) Appl. No.: 16/721,289

(22) Filed: Dec. 19, 2019

(65) Prior Publication Data

US 2021/0193331 A1 Jun. 24, 2021

(51) Int. Cl.
| | | |
|---|---|---|
| G16H 70/20 | (2018.01) | |
| G06F 16/51 | (2019.01) | |
| G16H 40/60 | (2018.01) | |
| G16H 30/40 | (2018.01) | |
| G16H 50/20 | (2018.01) | |

(52) U.S. Cl.
CPC ............ *G16H 70/20* (2018.01); *G06F 16/51* (2019.01); *G16H 30/40* (2018.01); *G16H 40/60* (2018.01); *G16H 50/20* (2018.01)

(58) Field of Classification Search
CPC .... G06F 1/00–2221/2153; G16H 10/00–80/00
See application file for complete search history.

(56) References Cited

U.S. PATENT DOCUMENTS

| | | | |
|---|---|---|---|
| 9,317,580 B2 | 4/2016 | Cohen-Solal | |
| 2009/0088620 A1* | 4/2009 | Zagorchev | G01T 1/1603 600/407 |
| 2009/0125334 A1* | 5/2009 | Krishnan | G16H 10/60 705/3 |

(Continued)

FOREIGN PATENT DOCUMENTS

| | | | | |
|---|---|---|---|---|
| EP | 1480154 A2 * | 11/2004 | ............. | G06F 19/28 |
| EP | 3503112 A1 * | 6/2019 | ............. | G16H 30/20 |

(Continued)

OTHER PUBLICATIONS

Lv et al., "Automatic spectral imaging protocol selection and iterative reconstruction in abdominal CT with reduced contrast agent dose: initial experience," Eur Radiol (2017) 27:374-383. (Year: 2017).*

(Continued)

*Primary Examiner* — Jonathon A. Szumny
(74) *Attorney, Agent, or Firm* — McCoy Russell LLP

(57) ABSTRACT

Methods and systems are provided for automated protocol recommendation and selection in a medical imaging system. In one example, a method may include receiving, from a hospital-specific user interface, a standard procedure ID, determining a medical imaging procedure based on the standard procedure ID, and, responsive to having previously received the standard procedure ID, generating one or more protocol recommendations based at least on the determined medical imaging procedure, and performing the determined medical imaging procedure based on at least one of the one or more protocol recommendations.

5 Claims, 5 Drawing Sheets

(56) References Cited

U.S. PATENT DOCUMENTS

| | | | | |
|---|---|---|---|---|
| 2011/0106563 A1* | 5/2011 | Kresl | .................... | G16H 20/10 |
| | | | | 705/3 |
| 2012/0271840 A1* | 10/2012 | Vosniak | ................. | G16H 50/20 |
| | | | | 707/E17.014 |
| 2013/0072781 A1* | 3/2013 | Omernick | ............. | G16H 30/20 |
| | | | | 600/410 |
| 2013/0208963 A1* | 8/2013 | Leal | ....................... | G16H 15/00 |
| | | | | 382/128 |
| 2016/0042146 A1* | 2/2016 | Douglass | ........... | G06Q 30/0631 |
| | | | | 705/3 |
| 2017/0316156 A1 | 11/2017 | Arima | | |
| 2018/0144823 A1* | 5/2018 | Raman | ................... | A61B 6/563 |
| 2018/0218127 A1* | 8/2018 | Salazar | .................. | G16H 50/30 |
| 2018/0322953 A1* | 11/2018 | Schmidt | ................ | G16H 50/70 |
| 2020/0098458 A1* | 3/2020 | West | ...................... | G16H 70/40 |
| 2020/0279635 A1* | 9/2020 | Letterie | ................. | G16H 10/40 |
| 2020/0380124 A1* | 12/2020 | Yavuz | .................. | G06F 21/562 |

FOREIGN PATENT DOCUMENTS

| | | | |
|---|---|---|---|
| JP | 2014505950 A | 3/2014 | |
| JP | 2017199286 A | 11/2017 | |
| WO | WO-2013179216 A2 * | 12/2013 | ........... G06F 19/321 |
| WO | WO-2017216356 A1 * | 12/2017 | ........... G06T 7/0012 |

OTHER PUBLICATIONS

JP application 2020-205154 filed Dec. 10, 2020—Office Action dated Mar. 30, 2022, Machine Translation; 6 pages.

\* cited by examiner

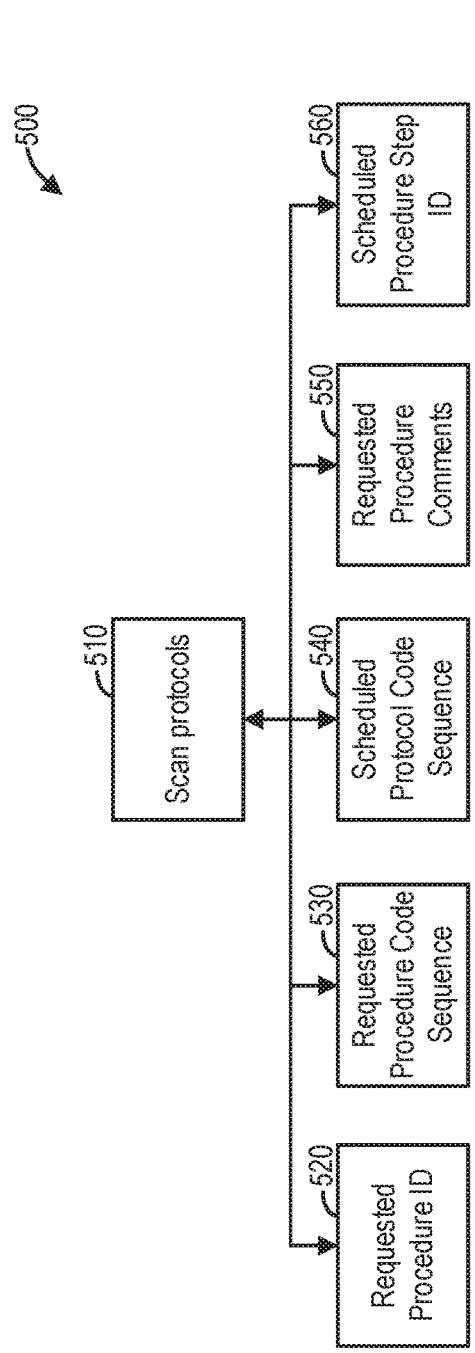
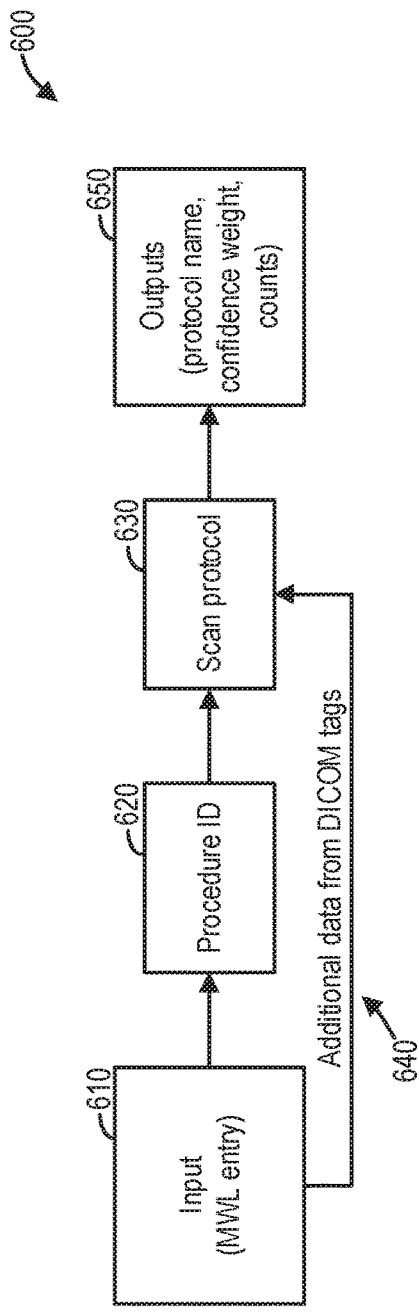
FIG. 5
FIG. 6

METHODS AND SYSTEMS FOR AUTOMATED SCAN PROTOCOL RECOMMENDATION

FIELD

Embodiments of the subject matter disclosed herein relate to medical imaging systems, and more particularly to systems and methods for automating recommendation of scan protocols based on local procedure identifiers.

BACKGROUND

An open technical problem in medical science is reproducibility, e.g., of medical care received at different medical facilities. The so-called "reproducibility crisis" not only results from biases held by individual medical professionals employed by the different medical facilities, but also from differing resources to which each medical facility has access. For example, a given medical facility may have access to scanners corresponding to any number of medical imaging modalities, each scanner manufactured by any one of a plurality of companies operating in the medical imaging space. As such, the given medical facility may implement local identifiers (e.g., alphanumeric codes) associated with various medical procedures to interface with the specific suite of medical imaging systems at the given medical facility. The local identifiers may also vary by medical facility, precluding facile standardization across all medical facilities and thereby reproducible medical treatment. For at least the aforementioned reasons, the so-called "reproducibility crisis" represents a significant and complex technical challenge in need of a technical solution.

BRIEF DESCRIPTION

In one embodiment, a method may include receiving, from a hospital-specific user interface, a standard procedure ID, determining a medical imaging procedure based on the standard procedure ID, and, responsive to having previously received the standard procedure ID, generating one or more protocol recommendations based at least on the determined medical imaging procedure, and performing the determined medical imaging procedure based on at least one of the one or more protocol recommendations.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIG. 5 shows a schematic block diagram of a correspondence between scan protocols and various exemplary standardized identifiers, according to an embodiment;

FIG. 6 shows a high-level input-output diagram for an intelligent automated protocoling system, according to an embodiment;

DETAILED DESCRIPTION

Figure 1:
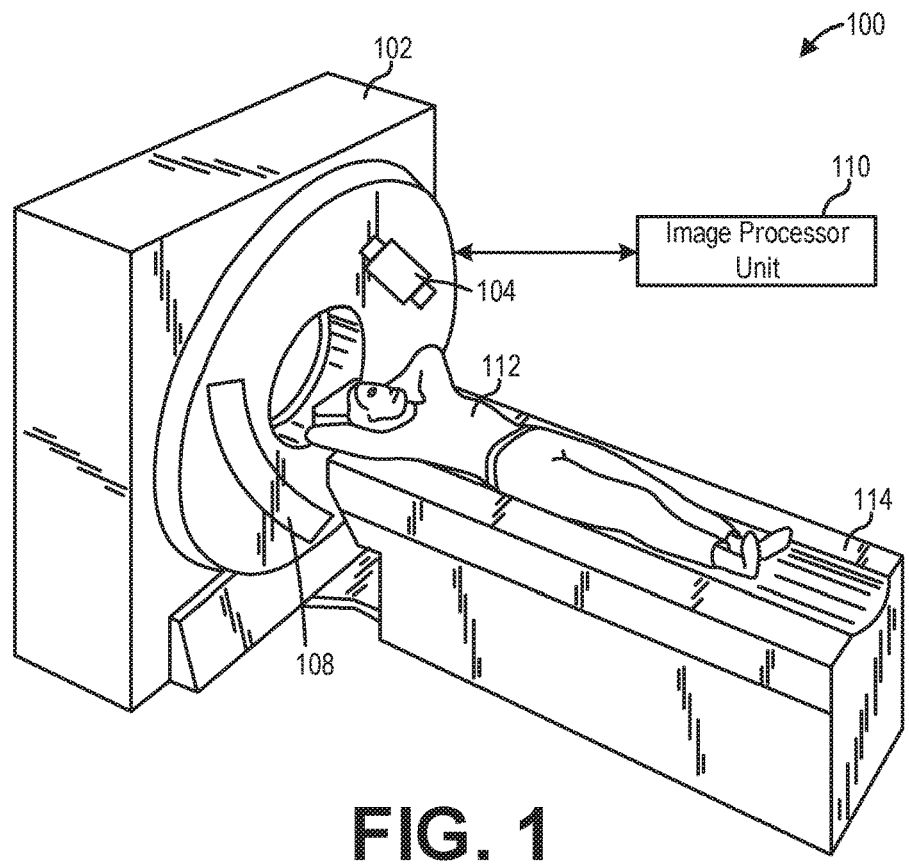
FIG. 1 shows a pictorial view of an exemplary medical imaging system, according to an embodiment.
Figure 2:
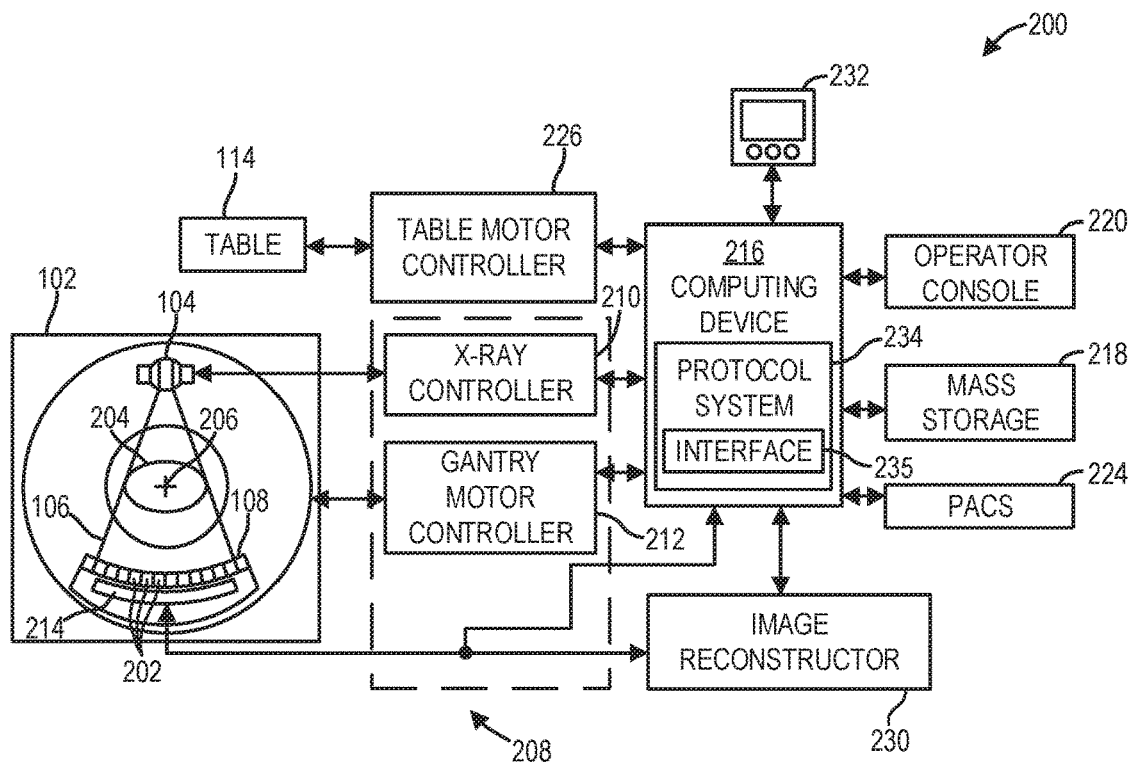
FIG. 2 shows a schematic block diagram of the exemplary medical imaging system, according to an embodiment.
Figure 4:
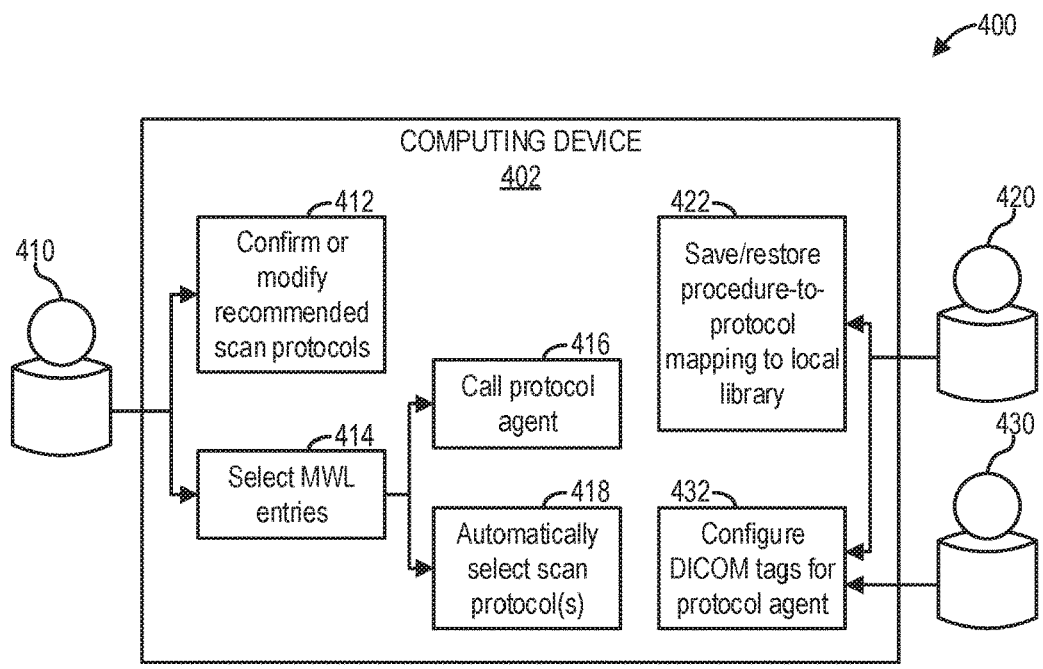
FIG. 4 shows a schematic block diagram of exemplary user interfaces for the exemplary computing device, according to an embodiment.

The following description relates to various embodiments of medical imaging systems, and automated protocol recommendation methods therefor. One such medical imaging system employing an intelligent automated protocoling system configured for such automated protocol recommendation is depicted in FIGS. 1 and 2. Various interfaces associated with the intelligent automated protocoling system for medical professionals, information technology (IT) managers, field engineers, and the like are depicted in FIG. 4.

Figure 3:
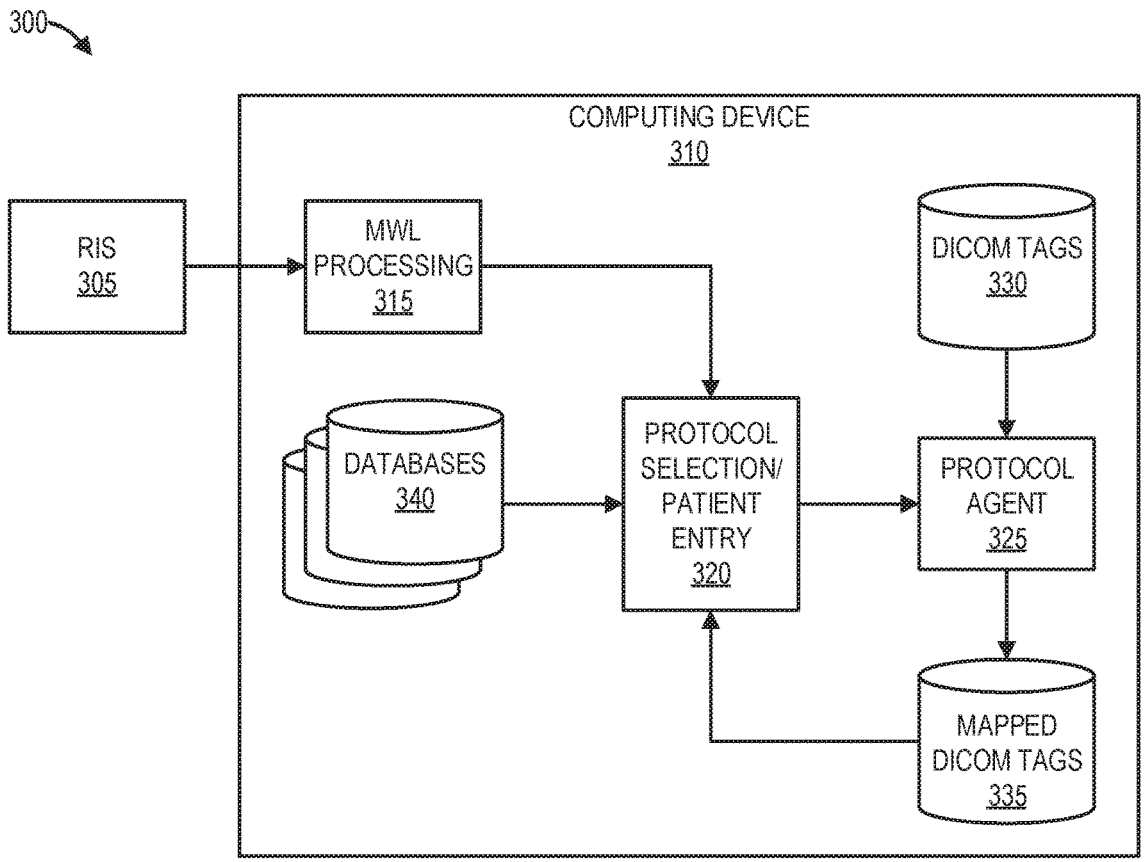
FIG. 3 shows a schematic block diagram of a high-level system architecture for an exemplary computing device, according to an embodiment.

The intelligent automated protocoling system may process modality worklist (MWL) entries and map standardized identifiers, e.g., Digital Imaging and Communications in Medicine (DICOM®) tags, thereto. A high-level system architecture and a high-level input-output diagram for such mapping are shown in FIGS. 3 and 6, respectively. The mapping may advantageously leverage known protocol-to-tag relationships, as shown in FIG. 5. The intelligent automated protocoling system may then employ the mapping to provide one or more protocol recommendations to a user of the medical imaging system. Accordingly, methods for selecting a scan protocol from the one or more protocol recommendations and executing a scan session based on the selected scan protocol are provided in FIGS. 7 and 8.

Referring now to FIG. 1, an exemplary imaging system 100 is depicted according to an embodiment. In the illustrated embodiment, the imaging system 100 is a computed tomography (CT) imaging system. However, it is understood that embodiments set forth herein may be implemented using other types of medical imaging modalities (e.g., x-ray, magnetic resonance (MR), ultrasound (US), positron emission tomography (PET), single-photon emission CT (SPECT), and combinations thereof, e.g., multi-modality imaging, such as PET/CT, PET/MR, SPECT/CT, etc.). Furthermore, it is understood that other embodiments do not actively acquire medical images. Instead, embodiments may retrieve images or imaging data that was previously acquired by an imaging system and analyze the imaging data as set forth herein.

The imaging system 100 may be configured to image a subject 112 such as a patient, an inanimate object, one or more manufactured parts, and/or foreign objects such as dental implants, stents, and/or contrast agents present within the body. In one embodiment, the imaging system 100 may include a gantry 102, which in turn, may further include at least one x-ray source 104 configured to project a beam of x-ray radiation 106 (see FIG. 2) for use in imaging the subject 112 laying on a table 114. Specifically, the x-ray source 104 may be configured to project the x-rays 106 towards a detector array 108 positioned on the opposite side of the gantry 102. Although FIG. 1 depicts only a single x-ray source 104, in certain embodiments, multiple x-ray sources and/or detectors may be employed to project a plurality of x-ray radiation beams 106 for acquiring projection data at different energy levels or angular orientations corresponding to the subject 112. In some embodiments, the x-ray source 104 may enable dual-energy gemstone spectral imaging (GSI) by rapid peak kilovoltage (kVp) switching. In some embodiments, the x-ray detector employed is a photon-counting detector which is capable of differentiating x-ray photons of different energies. In other embodiments, two sets of x-ray sources and detectors are used to generate dual-energy projections, with one set at low-kVp and the other at high-kVp. It should thus be appreciated that the methods described herein may be implemented with single energy acquisition techniques as well as dual energy acquisition techniques.

In certain embodiments, the imaging system 100 further includes an image processor unit 110 configured to reconstruct images of a target volume of the subject 112 using an iterative or analytic image reconstruction method, or a combination of both. For example, the image processor unit 110 may use an analytic image reconstruction approach such as filtered backprojection (FBP) to reconstruct images of a target volume of the patient. As another example, the image processor unit 110 may use an iterative image reconstruction approach such as advanced statistical iterative reconstruction (ASIR) or model-based iterative reconstruction (MBIR), and the like, to reconstruct images of a target volume of the subject 112. In some examples, the image processor unit 110 may use both an analytic image reconstruction approach such as FBP in addition to an iterative image reconstruction approach.

In some CT imaging system configurations, an x-ray source projects a cone-shaped x-ray radiation beam which is collimated to lie within an X-Y-Z plane of a Cartesian coordinate system and generally referred to as an "imaging plane." The x-ray radiation beam passes through an object being imaged, such as the patient or subject. The x-ray radiation beam, after being attenuated by the object, impinges upon an array of radiation detectors. The intensity of the attenuated x-ray radiation beam received at the detector array is dependent upon the attenuation of an x-ray radiation beam by the object. Each detector element of the array produces a separate electrical signal that is a measurement of the x-ray beam attenuation at the detector location. The attenuation measurements from all the detector elements are acquired separately to produce a transmission profile.

In some CT imaging systems, the x-ray source and the detector array are rotated with a gantry about the imaging plane and around the object to be imaged such that an angle at which the radiation beam intersects the object constantly changes. A group of x-ray radiation attenuation measurements, e.g., projection data, from the detector array at one angular position of the gantry is referred to as a "view." A "scan" of the object includes a set of views made at different angular positions, or view angles, during one revolution of the x-ray source and detector about the object. It is contemplated that the benefits of the methods described herein accrue to medical imaging modalities other than CT, so as used herein the term "view" is not limited to the use as described above with respect to projection data from one gantry angle. The term "view" is used to mean one data acquisition whenever there are multiple data acquisitions from different angles, whether from a CT, x-ray radiographic imaging, positron emission tomography (PET), or single-photon emission CT (SPECT) acquisition, and/or any other modality including modalities yet to be developed as well as combinations thereof in fused embodiments.

The projection data is processed to reconstruct an image that corresponds to one or more two-dimensional slices taken through the object or, in some examples where the projection data includes extended axial coverage, e.g., Z-axis illumination, a three-dimensional image volume of the object. One method for reconstructing an image from a set of projection data is referred to in the art as the filtered backprojection technique. Transmission and emission tomography reconstruction techniques also include statistical iterative methods such as maximum likelihood expectation maximization (MLEM) and ordered-subsets expectation maximization reconstruction techniques as well as iterative reconstruction techniques. This process converts the attenuation measurements from a scan into integers called "CT numbers" or "Hounsfield units," which are used to control the brightness of a corresponding pixel on a display device.

To reduce the total scan time, a "helical" scan may be performed. To perform a "helical" scan, the patient is moved while the data for the prescribed axial coverage is acquired. Such a system generates a single helix from a cone-beam helical scan. The helix mapped out by the cone beam yields projection data from which images in each prescribed slice may be reconstructed.

As used herein, the phrase "reconstructing an image" is not intended to exclude embodiments of the present invention in which data representing an image is generated but a viewable image is not. Therefore, as used herein, the term "image" broadly refers to both viewable images and data representing a viewable image. However, many embodiments generate (or are configured to generate) at least one viewable image.

Referring now to FIG. 2, an exemplary imaging system 200 similar to the imaging system 100 of FIG. 1 is depicted. That is, the imaging system 200 may be a CT imaging system. As shown, the imaging system 200 may include multiple components. The components may be coupled to one another to form a single structure, may be separate but located within a common room, or may be remotely located with respect to one another. For example, one or more of the modules described herein may operate in a data server that has a distinct and remote location with respect to other components of the imaging system 200.

In accordance with aspects of the present disclosure, the imaging system 200 may be configured for imaging a subject 204 (e.g., the subject 112 of FIG. 1). In one embodiment, the imaging system 200 may include the detector array 108 (see FIG. 1). The detector array 108 may further include a plurality of detector elements 202 that together sense the x-ray radiation beams 106 that pass through the subject 204 (such as a patient) to acquire corresponding projection data. Accordingly, in one embodiment, the detector array 108 may be fabricated in a multi-slice configuration including the plurality of rows of cells or detector elements 202. In such a configuration, one or more additional rows of the detector elements 202 may be arranged in a parallel configuration for acquiring the projection data.

In certain embodiments, the imaging system 200 may be configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the x-ray source 104 and the detector array 108 rotate, the detector array 108 may collect data of the attenuated x-ray beams. The data collected by the detector array 108 may undergo pre-processing and calibration to condition the data to represent the line integrals of the attenuation coefficients of the scanned subject 204. The processed data are commonly called projections.

The acquired sets of projection data may be used for basis material decomposition (BMD). During BMD, the measured projections may be converted to a set of density line-integral projections. The density line-integral projections may be reconstructed to form a density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the imaging system 200 may reveal internal features of the subject 204, expressed in the densities of two basis materials. The density image, or combinations of multiple density images, may be displayed to show these features. In traditional approaches to diagnosis of medical conditions, such as disease states, and more generally of medical events, a radiologist or physician would consider a hard copy or display of the density image, or combinations thereof, to discern characteristic features of interest. Such features might include lesions, sizes and shapes of particular anatomies or organs, and other features that would be discernable in the image based upon the skill and knowledge of the individual practitioner.

In one embodiment, the imaging system 200 may include a control mechanism 208 to control movement of the components such as rotation of the gantry 102 and the operation of the x-ray source 104. In certain embodiments, the control mechanism 208 may further include an x-ray controller 210 configured to provide power and timing signals to the x-ray source 104. Additionally, the control mechanism 208 may include a gantry motor controller 212 configured to control a rotational speed and/or position of the gantry 102 based on imaging requirements.

In certain embodiments, the control mechanism 208 may further include a data acquisition system (DAS) 214 configured to sample analog data received from the detector elements 202 and convert the analog data to digital signals for subsequent processing. For photon-counting imaging systems, the DAS 214 may download measured photon counts in one or more energy bins from detector array 108. The DAS 214 may be further configured to selectively aggregate analog data from a subset of the detector elements 202 into so-called macro-detectors, as described further herein.

The data sampled and digitized by the DAS 214 is transmitted to a computer or computing device 216. In the illustrated embodiment, the computing device 216 may be configured to interface with other components of the imaging system 200. As such, the computing device 216 may be configured to control operation of the imaging system 200.

In various embodiments, the computing device 216 may take the form of a mainframe computer, server computer, desktop computer, laptop computer, tablet device, network computing device, mobile computing device, mobile communication device, etc. In one embodiment, the computing device 216 may take the form of an edge device for interfacing between the various components of FIG. 2.

In some embodiments, the computing device 216 may store the data in a storage device or mass storage 218, either included in the computing device 216 or a separate device communicably coupled to the computing device 216. The storage device 218 may include removable media and/or built-in devices. Specifically, the storage device 218 may include one or more physical, non-transitory devices configured to hold data and/or instructions executable by the computing device 216 or the intelligent automated protocoling system 234 thereon to implement the herein described methods. Accordingly, when such methods are implemented, a state of the storage device 218 may be transformed (for example, to hold different, or altered, data). The storage device 218, for example, may include magnetoresistive random-access memory (MRAM), a hard disk drive, a floppy disk drive, a tape drive, a compact disk-read/write (CD-R/W) drive, a Digital Versatile Disc (DVD) drive, a high-definition DVD (HD-DVD) drive, a Blu-Ray drive, a flash drive, and/or a solid-state storage drive. In some embodiments, the intelligent automated protocoling system 234 and the storage device 218 may be integrated into one or more common devices, such as an application-specific integrated circuit or a system on a chip. It will be appreciated that the storage device 218 may be a non-transitory storage medium.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a physical keyboard, mouse, touchpad, and/or touch-screen to allow the operator to specify the commands and/or scanning parameters.

Although FIG. 2 illustrates only one operator console 220, more than one operator console may be coupled to the imaging system 200, for example, for inputting or outputting system parameters, requesting examinations, plotting data, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the imaging system 200 may either include, or is coupled to, a picture archiving and communications system (PACS) 224. In an exemplary implementation, the PACS 224 may further be coupled to a remote system such as a radiological information system (RIS), electronic health or medical records and/or hospital information systems (EHR/HIS), and/or to an internal or external network (not shown) to allow operators at different locations to supply commands and parameters and/or gain access to the image data.

The computing device 216 may use the operator-supplied and/or system-defined commands and parameters to operate a table motor controller 226, which in turn, may control a table 114 which may be a motorized table. Specifically, the table motor controller 226 may move the table 114 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. For example, one embodiment may use computing resources in a cloud network cluster for the image reconstructor 230.

In one embodiment, the image reconstructor 230 stores the images reconstructed in the storage device 218, either via the computing device 216 as shown in FIG. 2 or via a direct connection (not shown). Alternatively, the image reconstructor 230 may transmit the reconstructed images to the computing device 216 for generating useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

The various methods or processes (such as the methods described below with reference to FIGS. 7 and 8) described further herein may be stored as executable instructions in non-transitory memory on a computing device (or controller) in the imaging system 200. In one embodiment, the image reconstructor 230 may include such executable instructions in non-transitory memory, and may apply the methods described herein to reconstruct an image from scanning data. In another embodiment, the computing device 216 may include the instructions in non-transitory memory, and may apply the methods described herein, at least in part, to a reconstructed image after receiving the reconstructed image from the image reconstructor 230. In yet another embodiment, the methods and processes described herein may be distributed across the image reconstructor 230 and the computing device 216.

In operation, the computing device 216 may acquire imaging data and other medical data, which may be translated for display to a user (e.g., a medical professional) on the display device 232. As an example, the medical data may be transformed into and displayed at the display device 232 as a user-facing graphical and/or textual format, which may be standardized across all implementations of the imaging system 200 or may be particular to a given facility, department, profession, or individual user. As another example, the imaging data (e.g., three-dimensional (3D) volumetric data sets, two-dimensional (2D) imaging slices, etc.) may be used to generate one or more images at the computing device 216, which may then be displayed to the operator or user at the display device 232. As such, the display device 232 may allow the operator to evaluate the imaged anatomy. The display device 232 may also allow the operator to select a volume of interest (VOI) and/or request patient information, for example, via a graphical user interface (GUI) for a subsequent scan or processing.

In embodiments described herein, the computing device 216 may store an intelligent automated protocoling system 234 thereon, which may interface with various components of the imaging system 200 via an interface 235. Specifically, the intelligent automated protocoling system 234 may be configured to automatically recommend scan protocols based on received medical data. Further, the intelligent automated protocoling system 234 may be operable to translate the selected scan protocols to scan protocol executables for initiating a scan session. In some embodiments, the intelligent automated protocoling system 234 may automatically recommend, select, and translate the scan protocols for initiating the scan session upon receiving an input including the medical data (e.g., a MWL entry, a local procedure ID, etc.). In additional or alternative embodiments, the intelligent automated protocoling system 234 may recommend and display scan protocols (e.g., at the display device 232) and may then await confirmation from a user, e.g., at the operator console 220, for selection and/or translation of the recommended protocols. In some examples, the user may instead enter a manual selection from the one or more protocol recommendations into the operator console 220 or may manually select another scan protocol entirely (e.g., not included in the one or more protocol recommendations). The intelligent automated protocoling system 234 may accordingly include the interface 235 for receiving and transmitting the medical data and the recommended scan protocols or scan protocol executables.

The intelligent automated protocoling system 234 may take the form of a logic subsystem including one or more physical devices configured to execute one or more instructions. For example, the intelligent automated protocoling system 234 may be configured to execute one or more instructions that are part of one or more applications services, programs, routines, libraries, objects, components, data structures, or other logical constructs. Such instructions may be implemented to perform a task, implement a data type, transform a state of one or more devices, or otherwise arrive at a desired result.

The intelligent automated protocoling system 234 may include one or more processors configured to execute software instructions. In additional or alternative embodiments, the intelligent automated protocoling system 234 may include one or more hardware or firmware logic machines configured to execute hardware or firmware instructions. The one or more processors may be single- or multi-core, and programs executed thereon may be configured for serial or parallel or distributed processing. The intelligent automated protocoling system 234 may optionally include individual components distributed throughout two or more devices corresponding to the computing device 216, where the two or more devices may be remotely located and/or configured for coordinated processing. Further, one or more aspects of the intelligent automated protocoling system 234 may be virtualized and executed by remotely accessible networked computing device configured in a cloud computing configuration.

The intelligent automated protocoling system 234 may receive the medical data as provided by a user of the imaging system 200 (e.g., at the operator console 220), from the PACS 224, or from a remote device storing another IT system (e.g., an EHR/HIS, RIS, etc.) and scan protocols from a master protocol library, whereby the intelligent automated protocoling system 234 may automatically generate one or more protocol recommendations. In some embodiments, the master protocol library may be stored on the storage device 218. In other embodiments, the master protocol library may be stored on another longer-term storage device or network (not shown at FIG. 2), such as a cloud-based computing device or server. However, it will be appreciated that the master protocol library may be stored on any known data storage medium, for example, a permanent storage medium, removable storage medium, and the like. As such, it will be appreciated that the master protocol library may be stored on a non-transitory storage medium. It will be appreciated that other remote devices (not shown at FIG. 2) may have access to the master protocol library, such that the remote device may be configured to periodically update the master protocol library by adding, removing, substituting, or otherwise altering the scan protocols stored in the master protocol library.

Upon receiving a subset of scan protocols from the master library, the intelligent automated protocoling system 234 may recommend scan protocols for selection and execution as scan protocol executables, such that scan sessions may be initiated therefrom. In some embodiments, the user may instead manually query a scan protocol, which may be directly received by the computing device 216 from the master protocol library, which may be translated to the scan protocol executable from which the scan session may be initiated. It will be appreciated that when a scan protocol has been selected and executed as a scan protocol executable, regardless of whether the scan protocol has been recommended by the intelligent automated protocoling system 234 or the scan protocol has been manually provided by the user, the intelligent automated protocoling system 234 may update a local procedure-to-protocol mapping library (e.g., stored on the storage device 218) based on the selected scan protocol.

In general, numerous manual steps are inherent to a workflow for selecting a scan protocol, initiating a scan session based on the scan protocol, and acquiring images therefrom. Further, a level of experience in selecting the scan protocol may not only vary by individual or profession, but also by medical facility, such that there may exist geographic variability in scanning proficiency and consistency. Additionally, each medical facility may implement local procedure identifiers, which may include various incompatible alphanumeric formats. Each of the above considerations may introduce variability into the workflow, thereby resulting in inconsistent treatment for substantially similar medical cases.

However, the inventors have herein recognized that, though the various alphanumeric formats may be incompatible with one another, the local procedure identifiers may nonetheless key to substantially similar scan protocols. Further, additional standards may be implemented which are not specific to any given medical facility. For example, the DICOM® standard is widely used across medical facilities for communicating and managing imaging data in a consistent manner.

According to the embodiments disclosed herein, the above-described issues may be at least partly addressed by methods and systems for automated scan protocol recommendation and selection. For example, an intelligent automated protocoling system may be included in a medical imaging system, where the intelligent automated protocoling system may be configured to automatically generate protocol recommendations for a given query (e.g., an MWL entry) such that a user of the medical imaging system may select a scan protocol with increased consistency, concomitantly improving selection accuracy and imaging quality. The intelligent automated protocoling system may further be configured to update a local procedure-to-protocol mapping library based on the selection. Specifically, the intelligent automated protocoling system may leverage substantially similar scan protocols which are present across medical facilities by determining like DICOM® MWL tags underlying the similar scan protocols. As such, the DICOM® MWL tags may function as a "lingua franca" for mapping of local procedure identifiers to scan protocols. In this way, the intelligent automated protocoling system may adaptively learn based on incremental updating of procedure-to-protocol mapping, such that more consistent protocol recommendations may be generated for similar medical cases over time regardless of geographic location or specific medical facility.

Referring now to FIG. 3, a schematic block diagram 300 is depicted, showing a high-level system architecture for an exemplary computing device 310. Specifically, the computing device 310 may receive MWL entries from an RIS 305, whereby the MWL entries may be used in routines for automatically generating protocol recommendations. In exemplary embodiments, the computing device 310 may be the computing device 216 of FIG. 2. Further, it will be appreciated that at least some of the components discussed with reference to FIG. 3 (e.g., MWL processing module 315, protocol selection and patient entry module 320, protocol agent 325) may correspond to the intelligent automated protocoling system 234 of FIG. 2.

As shown, the RIS 305 may be communicably coupled to the computing device 310, where the RIS 305 may be remotely located from the computing device 310 (e.g., the RIS 305 may be accessed via a wired or wireless network). The RIS 305 may store MWL entries corresponding to various scan protocols. Accordingly, one or more MWL entries may be queried by a user and automatically retrieved from the RIS 305 and transmitted to an MWL processing module 315.

At the MWL processing module 315, the queried MWL entries may be translated into, or correlated with, a local procedure identifier (ID). The local procedure ID may be rendered in a hospital-specific format and may correspond to scan protocols specific to imaging modalities at a given medical facility (e.g., hospital). It will be appreciated that, in some embodiments, the MWL processing module 315 may collect an initial dataset of MWL entries correlated to local procedure IDs based on prior executed scan sessions. As such, the MWL processing module 315 may determine the local procedure IDs which correspond to the queried MWL entries based on the initial dataset. It will further be appreciated that, as additional scan sessions are executed, the initial dataset may be periodically updated based on more recent imaging procedures.

After correlation/translation of the queried MWL entries to the local procedure IDs, a protocol selection and patient entry module 320 may log patient-specific medical data from the queried MWL entries and the local procedure IDs in a patient database (e.g., one of databases 340). The patient database may include a plurality of patient profiles respectively including the patient-specific medical data from the queried MWL entries, as well as current and prior local procedure IDs correlated to the patient-specific medical data. In this way, the high-level system architecture depicted by FIG. 3 may account for individualized medical histories and prior exams.

The protocol agent 325 may then map DICOM® tags to the local procedure IDs. Specifically, the protocol agent 325 may be communicably coupled to a DICOM® tag database 330, whereon a master list of DICOM® tags may be stored. Accordingly, the protocol agent 325 may receive a plurality of DICOM® tags, at least some of which may be mapped to local procedure IDs based on prior correlations. For example, a particular local procedure ID may key to a medical procedure which employs one or more particular DICOM® tags. Once the protocol agent 325 has mapped the local procedure IDs to corresponding DICOM® tags, a mapped DICOM® tags database 335 may be updated. In some examples, newly-mapped DICOM® tags may be added to the mapped DICOM® tags database 335. However, in additional or alternative examples, at least some mapped DICOM® tags already stored in the mapped DICOM® tags database 335 may be updated based on updates to the local procedure IDs (that is, a given medical procedure may be altered or updated).

As shown, the mapped DICOM® tags from the mapped DICOM® tags database 335 may be transmitted to the protocol selection and patient entry module 320. Thereat, the protocol selection and patient entry module 320 may accordingly update a corresponding patient profile with the mapped DICOM® tags. For example, the patient profile may be associated with a particular local procedure ID, and the DICOM® tags mapped thereto may accordingly be linked to the patient profile. It will therefore be appreciated that the patient profiles stored on the patient database may be updated asynchronously relative to the MWL entries stored on the RIS 305. As such, a given implementation of the computing device 310, and the automated protocoling routines stored thereon, may be customized to a particular medical facility as patient profiles are updated based on prior local procedure IDs employed therefor.

Further, the mapped DICOM® tags may be employed to improve a consistency of protocol recommendations. For example, a plurality of scan protocols may be retrieved from a master protocol library (e.g., one of the databases 340), where each of the plurality of scan protocols may also be mapped to a set of DICOM® tags. As such, the set of DICOM® tags mapped to the retrieved scan protocols may then be searched for a match to the DICOM® tags mapped to the local procedure IDs corresponding to the queried MWL entries. The protocol selection and patient entry module 320 may then recommend one or more scan protocols which correspond to the local procedure IDs, and therefore to the particular patient and the queried MWL entries therefor. In some embodiments, each of the retrieved scan protocols may be assigned a confidence weight based on a strength of a match to a corresponding local procedure ID, such that scan protocols having relatively high confidence weights (e.g., having confidence weights greater than a threshold confidence weight) may be recommended. Accordingly, a local procedure-to-protocol mapping library (e.g., one of the databases 340) may be constructed based on mapping of the local procedure IDs to the recommended scan protocols. In some examples where local procedure IDs are already mapped to one or more scan protocols, the local procedure-to-protocol mapping library may be accessed without further mapping from the protocol agent 325. However, the local procedure-to-protocol mapping library may be updated based on a number of instances that a particular local procedure ID is determined and/or a particular scan protocol is recommended. In this way, though automated protocoling may be adapted to local procedure IDs implemented at a particular medical facility, similar scan protocols may be recommended across medical facilities based on standardized DICOM® tags. As such, a consistency of automated protocol recommendation may be improved regardless of location, concomitantly improving patient experience and health outcomes.

It will be appreciated that, in some embodiments, the databases 340 may include one or more databases stored locally at the computing device 310. However, in additional or alternative embodiments, at least some of the one or more databases included in the databases 340 may be stored at a remote device (not shown at FIG. 3) and may be accessed via a wired or wireless network. It will further be appreciated that other databases and libraries beyond the patient database, master protocol library, and local procedure-to-protocol mapping library may be contemplated within the scope of the present disclosure.

Referring now to FIG. 4, a schematic block diagram 400 is depicted, showing exemplary user interfaces for an exemplary computing device 402. Specifically, the computing device 402 may provide different user interfaces, each user interface tailored to a medical imaging role of a given user. For example, users of the computing device 402 may include medical professionals 410, field engineers 420, and IT managers 430, whereby one of the tailored user interfaces may be provided for each type of user. In exemplary embodiments, the computing device 402 may be the computing device 216 of FIG. 2 and/or the computing device 310 of FIG. 3. Further, it will be appreciated that at least some of the processes discussed with reference to FIG. 4 may correspond to actions of the intelligent automated protocoling system 234 of FIG. 2. In this way, a computing device implementing an intelligent automated protocoling system may be configured for various use cases by providing different user interfaces for users having different medical imaging roles.

As a first example, the user may be the medical professional 410. At 414, the computing device 402 may enable the medical professional 410 to select or query MWL entries, e.g., from a RIS (not shown at FIG. 4). The MWL entries may correspond to medical procedure ordered for a specific patient requesting medical care from the medical professional 410 (or from another medical professional in communication with the medical professional 410). Upon selection of the MWL entries, the computing device 402 may be configure to determine whether a local procedure-to-protocol mapping library has mapped the medical procedure (e.g., keyed to a local procedure ID) to one or more scan protocols. If such a mapping does not exist, or requires updating, a protocol agent (e.g., the protocol agent 325 of FIG. 3) may be called to map the MWL entries (or local procedure IDs keyed thereto) to DICOM® tags. Since the one or more scan protocols may also be mapped to DICOM® tags, the one or more scan protocols may be matched to the MWL entries, and thereby the medical procedure, based on like DICOM® tags. Thus, at 418, the computing device 402 may be configured to automatically recommend the one or more scan protocols and select a scan protocol therefrom for initiating a scan session. Once the one or more scan protocols have been recommended, the medical professional 410 may then, at 412, confirm or modify the one or more recommended scan protocols and/or the automatically selected scan protocol.

As a second example, the user may be the field engineer 420. At 422, the computing device 402 may enable the field engineer 420 to save or restore procedure-to-protocol mappings to the local procedure-to-protocol mapping library. For example, the field engineer 420 may provide procedure-to-protocol mappings acquired from another computing device (e.g., a computing device including an intelligent automated protocoling system which may have already accumulated sufficient mapping data to accurately and consistently provide protocol recommendations). As such, the procedure-to-protocol mappings provided by the field engineer 420 may enable accuracy and consistency across computing devices.

As a third example, the user may be the IT manager 430. At 432, the computing device 402 may enable the IT manager 430 to configure DICOM® tags for the protocol agent (e.g., the protocol agent 325 of FIG. 3). For example, the IT manager 430 may add DICOM® tags to a DICOM® tag database (e.g., the DICOM® tag database 330 of FIG. 3) or may update the DICOM® tag database. It will be appreciated that the computing device 402 may also enable the field engineer 420 to configure DICOM® tags for the protocol agent.

Referring now to FIG. 5, a schematic block diagram 500 is depicted, showing a correspondence between one or more scan protocols 510 and various exemplary DICOM® tags, where the exemplary DICOM® tags may include Requested Procedure ID 520 (e.g., DICOM® tag (0040,1001)), Requested Procedure Code Sequence 530 (e.g., DICOM® tag (0032,1064)), Schedule Protocol Code Sequence 540 (e.g., DICOM® tag (0040,0008)), Requested Procedure Comments 550 (e.g., DICOM® tag (0040,1400)), and Scheduled Procedure Step ID 560 (e.g., DICOM® tag (0040,0009)). In some embodiments, the correspondence may be one-to-many, such that a single scan protocol 510 may correspond to sets or sequences of DICOM® tags. A computing device (e.g., the computing device 216 of FIG. 2) implementing an intelligent automated protocoling system (e.g., the intelligent automated protocoling system 234 of FIG. 2) may be enabled to uniquely map sets of DICOM® tags to individual scan protocols. Further, local procedure IDs at a particular medical facility may be mapped to similar sets of DICOM® tags. In specific examples, the particular medical facility may favor a particular one or more of the exemplary DICOM® tags, such that local procedure IDs commonly map to the particular one or more DICOM® tags. As such, known correspondences (e.g., at particular medical facilities or across medical facilities) may be leveraged for matching the scan protocols to the local procedure IDs by way of common DICOM® tags therebetween.

Referring now to FIG. 6, a high-level input-output diagram 600 for an intelligent automated protocoling system (e.g., the intelligent automated protocoling system 234 of FIG. 2) is depicted. Specifically, an input 610, such as one or more MWL entries, may be received at the intelligent automated protocoling system. The input 610 may then be mapped to a local procedure ID 620, after which the local procedure ID 620 may be mapped to a scan protocol 630. Such procedure-to-protocol mapping may be performed by matching pairs of like DICOM® tags associated with each of the local procedure ID 620 and the scan protocol 630, such that the DICOM® tags may serve as a "lingua franca" to link the local procedure ID 620 to the scan protocol 630. It will be appreciated that additional data 640 from DICOM® tags associated with the input 610 may be employed to further refine the procedure-to-protocol mapping. For example, in some embodiments, the additional data may include raw text which may be utilized in a semantic search algorithm to confirm mapping of the local procedure ID 620 to the scan protocol 630. After the scan protocol 630 has been determined based on the procedure-to-protocol mapping, an output 650 may be generated. The output 650 may include a variety of data structures associated with the scan protocol 630, such as a protocol name, a confidence weight based on a level of confidence in the procedure-to-protocol mapping, and selection count(s) corresponding to a number of times that the scan protocol 630 has been selected and translated to a scan session executable for a given patient, a given group of similar patients, and/or a given medical facility.

Figure 7:
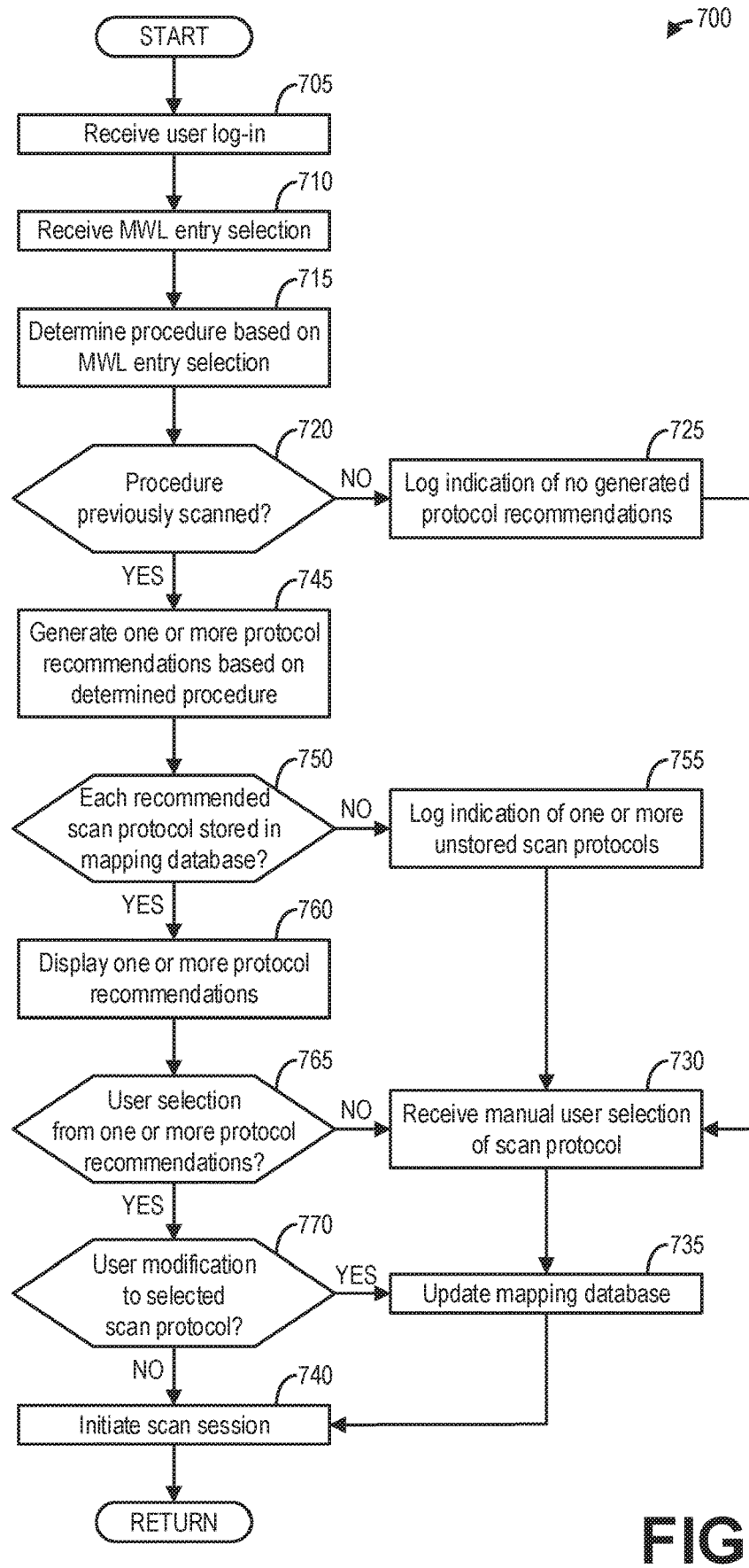
FIG. 7 shows a flow chart of a method for recommending and selecting a scan protocol, and executing a scan session based on the selected scan protocol, according to an embodiment.
Figure 8:
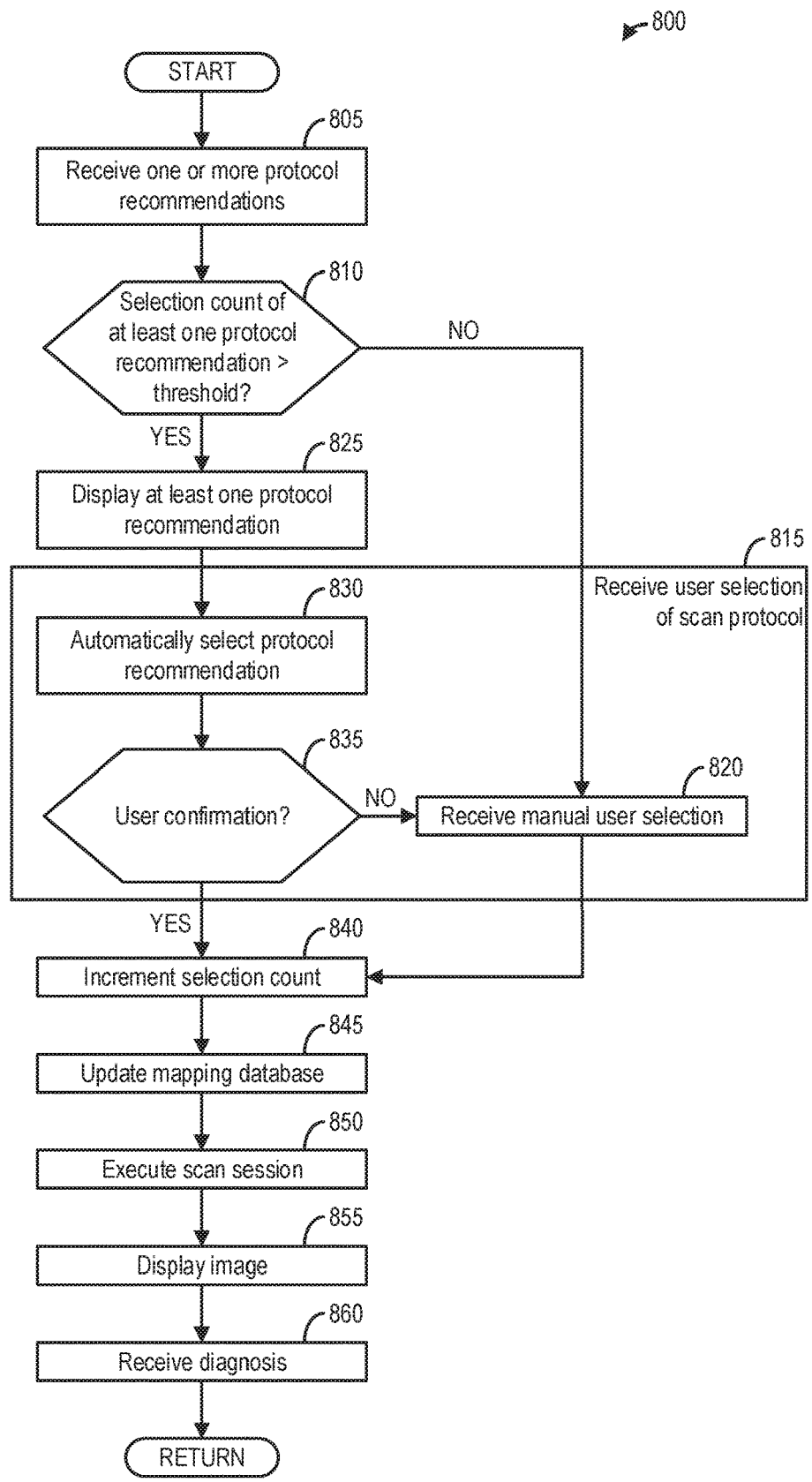
FIG. 8 shows a flow chart of a method for, upon receiving one or more protocol recommendations, selecting a scan protocol and executing a scan session based on the selected scan protocol, according to an embodiment.

Referring now to FIGS. 7 and 8, methods are depicted for generating protocol recommendations with an intelligent automated protocoling system implemented in a medical imaging system, selecting a scan protocol based on the generated protocol recommendations, and executing a scan session based on the selected scan protocol. The methods of FIGS. 7 and 8 (e.g., methods 700, 800) are described below with regard to the systems and components depicted in FIGS. 1 and 2. For example, the medical imaging system and the intelligent automated protocoling system may be the imaging system 200 and the intelligent automated protocoling system 234 of FIG. 2, respectively. However, it will be appreciated that the method of FIGS. 7 and 8 may be implemented with other systems and components without departing from the scope of the present disclosure. In some embodiments, the methods of FIGS. 7 and 8 may be implemented as executable instructions in any of the medical imaging systems described with reference to FIGS. 1 and 2. In one embodiment, the methods of FIGS. 7 and 8 may be implemented in non-transitory memory of a computing device, such as the computing device 216 of the imaging system 200 in FIG. 2. It will further be appreciated that individual steps discussed with reference to the methods of FIGS. 7 and 8 may be added, removed, substituted, or interchanged within the scope of the present disclosure.

Referring now to FIG. 7, a flow chart is depicted, showing a method 700 for recommending and selecting a scan protocol with the intelligent automated protocoling system, and executing a scan session based on the selected scan protocol. Specifically, a user may provide a MWL entry selection from which one or more protocol recommendations may be generated and displayed to the user. Upon receiving a user selection of a scan protocol (e.g., corresponding to one of the one or more protocol recommendations or a manually provided scan protocol), the selected scan protocol may then be translated to a scan session executable which may be utilized to initiate the scan session.

Method 700 may begin at 705, where a user log-in may be received. The user log-in may correspond to a plurality of user log-in credentials, such as a username and password, which may then be validated. During or upon validation, the intelligent automated protocoling system may associate each user with a specific medical imaging role (e.g., medical professional, field engineer, IT manager, etc.) and may present a different user interface depending on the specific medical imaging role. For example, inputs received in method 700 may be provided by a medical professional to a user interface tailored to the medical professional. It will further be appreciated that the user interface may be specific to a given medical facility (e.g., hospital) with which the user is associated.

At 710, method 700 may include receiving an MWL entry selection from the user. Specifically, the user may select or query one or more MWL entries from an IT system, such as an RIS. Further, the one or more MWL entries may correspond to a specific patient having a medical issue.

At 715, method 700 may include determining a medical imaging procedure based on the MWL entry selection. For example, one or more local procedure IDs may be correlated to the one or more MWL entries in the MWL entry selection. Each of the one or more local procedure IDs may further correspond to a specific medical imaging procedure.

At 720, method 700 may include determining whether the medical imaging procedure has been previously scanned. Specifically, the one or more local procedure IDs may be mapped to a set of DICOM® tags. Further, one or more scan protocols may be mapped to a similar set of DICOM® tags. The one or more local procedure IDs may then be mapped to the one or more scan protocols based on like DICOM® tags to build a mapping database (e.g., a local procedure-to-protocol mapping library). As such, if each of the one or more local procedure IDs and the one or more scan protocols correspond to a previously scanned medical imaging procedure, then the intelligent automated protocoling system may simply query the local procedure-to-protocol mapping library. It will be appreciated that, in some embodiments, the local procedure-to-protocol mapping library may be updated only when a given medical imaging procedure has been selected and executed a threshold number of times (as discussed in detail below with reference to method 800 of FIG. 8). Thus, in such embodiments, the medical imaging procedure may have been previously scanned, but may not be logged in the local procedure-to-protocol mapping library.

If the medical imaging procedure has not been previously scanned, method 700 may proceed to 725 to log an indication that no protocol recommendations were generated by the intelligent automated protocoling system. A notification based on the indication may then be generated and displayed to the user at a display device of the medical imaging system.

At 730, method 700 may include receiving a manual user selection of a scan protocol. Since the user has not selected a protocol recommendation (e.g., because no protocol recommendations were generated by the intelligent automated protocoling system), the user may instead manually provide the scan protocol to the intelligent automated protocoling system. Then, at 735, method 700 may include updating the mapping database (e.g., the local procedure-to-protocol mapping library) based on the manual user selection. In some embodiments, each scan protocol may be associated with a selection count, whereby the selection count may be incremented by one each time the scan protocol is selected (manually or otherwise). Accordingly, the local procedure-to-protocol mapping library may also be updated with the incremented selection count. However, in other embodiments, the local procedure-to-protocol mapping library may only be updated when the selection count is greater than a threshold selection count. At 740, method 700 may then include initiating a scan session (e.g., a medical imaging scan) based on the selected scan protocol. Specifically, the intelligent automated protocoling system may translate the selected scan protocol to a scan protocol executable, which may then be executed by the medical imaging system as the scan session. Method 700 may then end.

Returning to 720, if the medical imaging procedure has been previously scanned, method 700 may proceed to 745 to automatically generate one or more protocol recommendations based on the determined medical imaging procedure. Specifically, the intelligent automated protocoling system may access the local procedure-to-protocol mapping library to determine which scan protocols have been previously mapped to the medical imaging procedure. In some embodiments, the intelligent automated protocoling system may employ additional data (e.g., searchable text, etc.) from DICOM® tags corresponding to the MWL entry selection to further refine the procedure-to-protocol mapping and the one or more protocol recommendations therefrom.

At 750, method 700 may include determining whether each of the one or more protocol recommendations corresponds to a scan protocol stored in the mapping database (e.g., the local procedure-to-protocol mapping library). If at least one of the one or more protocol recommendations is not found in the local procedure-to-protocol mapping library, method 700 may proceed to 755 to log an indication that one or more of the scan protocols are not stored in the local procedure-to-protocol mapping library. In such cases, since no protocol recommendations are provided to the user, method 700 may then proceed to 730 (as described above).

If each of the one or more protocol recommendation is found in the local procedure-to-protocol mapping library, method 700 may proceed to 760 to display the one or more protocol recommendations at the display device. In some embodiments, the intelligent automated protocoling system may provide only the one or more protocol recommendations for display at the display device. However, in other embodiments, the intelligent automated protocoling system may provide additional information, such as confidence weights, selection counts, etc. to aid in a user selection of a scan protocol from the one or more protocol recommendations. In additional or alternative embodiments, the intelligent automated protocoling system may prompt the user with an automated selection of a scan protocol from the one or more protocol recommendations. For example, the intelligent automated protocoling system may automatically select a recommended scan protocol having a highest confidence weight or a highest selection count. It will be appreciated that no automated selection of the scan protocol may be made in examples wherein no "most likely" scan protocol (e.g., having the highest confidence weight or the highest selection count) may be determined from the one or more protocol recommendations (that is, the intelligent automated protocoling system may not "arbitrarily" select the scan protocol from the one or more protocol recommendations).

At 765, method 700 may include determining whether the user selection of the scan protocol from the one or more protocol recommendations has been received. In some embodiments, receiving the user selection may include receiving a manual user selection of a scan protocol from the one or more displayed protocol recommendations. However, in embodiments wherein the intelligent automated protocoling system prompts the user with an automatically selected scan protocol, receiving the user selection may include receiving a user confirmation of the automatically selected scan protocol. If the user selection is not received, since no protocol recommendations are selected by the user, method 700 may proceed to 730 (as described above).

If the user selection is received (e.g., the manual user selection from the one or more protocol recommendations or the user confirmation of the automatically selected scan protocol), method 700 may proceed to 770 to determine whether a user modification to the selected scan protocol has been received. If the user modification has been received, method 700 may then proceed to 735 to update the mapping database (e.g., the local procedure-to-protocol mapping library) based on the user modification. In some embodiments, a selection count corresponding to a user-modified scan protocol may be reset so as to account for the user modification. In this way, the intelligent automated protocoling system may take into account modifications to the scan protocols for future recommendation and selection.

If no user modification is received, or if the local procedure-to-protocol mapping library has been updated with the received user modification (e.g., at 735), method 700 may proceed to 740 to initiate the scan session based on the selected scan protocol. Specifically, the intelligent automated protocoling system may translate the selected scan protocol (whether modified by the user or not) to the scan protocol executable, which may then be executed by the medical imaging system as the scan session. Method 700 may then end.

Referring now to FIG. 8, a flow chart is depicted, showing a method 800 for selecting a scan protocol from one or more protocol recommendations and executing a scan session based on the selected scan protocol. Specifically, selection of the scan protocol may depend at least in part upon previous selections made by a user (e.g., a medical professional) operating a medical imaging system including an intelligent automated protocoling system implemented thereon. Following selection of the scan protocol, the scan session corresponding to the selected scan protocol may be executed such that an image may be displayed and a diagnosis of a medical issue may be received based on the displayed image.

Method 800 may begin at 805, where one or more protocol recommendations may be received from a mapping database (e.g., a local procedure-to-protocol mapping library). Each of the one or more protocol recommendations may correspond to a scan protocol determined by the intelligent automated protocoling system to match with a queried medical imaging procedure. In some embodiments, each of the one or more protocol recommendations may be assigned a confidence weight, the confidence weight determined based on a level of confidence in the match between the corresponding scan protocol and the queried medical imaging procedure.

At 810, method 800 may include determining whether a selection count of at least one protocol recommendations of the one or more protocol recommendations is greater than a threshold selection count. In some embodiments, the selection count of a given protocol recommendation may be a total number of instances in which a scan protocol corresponding to the given protocol recommendation was selected over a predetermined duration, or since the intelligent automated protocoling system was initially actuated. In other embodiments, the selection count of the given protocol recommendation may be an average selection count, wherein the average selection count may be determined by a linear weighted moving average (LWMA). Specifically, the LWMA may be based on confidence weights associated with the at least one protocol recommendations, where the confidence weights may be based on segments of selection counts over the predetermined duration. In one embodiment, each of the segments may include 20 selection counts and the predetermined duration may be 12 months. In additional or alternative embodiments, the selection counts may be specific to a patient, a subset of similar patients, or a medical facility, such that the intelligent automated protocoling system may generate customized protocol recommendations.

If no selection count of any of the one or more protocol recommendations is greater than the threshold selection count, then method 800 may proceed to 815 to receive a user selection of a scan protocol. Specifically, receiving the user selection may include, at 820, receiving a manual user selection of the scan protocol. That is, since none of the selection counts of the one or more protocol recommendations exceeded the threshold selection count, no protocol recommendation may be displayed to the user, and the manual selection may be provided as an alternative to a selection from the one or more protocol recommendations. In some embodiments, however, an indication may be generated informing the user of a failure of the one or more generated protocol recommendations to be selected a threshold number of instances to be displayed to the user.

If the selection count of the at least one protocol recommendations is greater than the threshold selection count, then method 800 may proceed to 825 to display the at least one protocol recommendations at a display device of the medical imaging system. As such, if a given protocol recommendation is generated by the intelligent automated protocoling system, the given protocol recommendation may only be displayed to a user of the medical imaging system if a selection count therefor has exceeded the threshold selection count. In this way, the intelligent automated protocoling system may be less likely to recommend scan protocols inconsistent with scan protocols previously selected (whether automatically, e.g., by the intelligent automated protocoling system, or manually, e.g., by the user of medical imaging system). In some embodiments, further information relating to the one or more protocol recommendations may be provided to the user to aid in the user selection of the scan protocol from the one or more protocol recommendations.

In some embodiments, the at least one protocol recommendations may be displayed as a sorted list. As an example, the sorted list may be sorted by selection count, such that a protocol recommendation having a highest selection count may be displayed at a top of the sorted list. As an example, the sorted list may be sorted by confidence weight, such that a protocol recommendation having a highest confidence weight may be displayed at the top of the sorted list. In additional or alternative embodiments, only a maximum number of protocol recommendations may be displayed. For example, up to six protocol recommendations of the at least one protocol recommendations (e.g., protocol recommendations having highest confidence weights of the at least one protocol recommendations) may be displayed at the display device.

At 815, method 800 may include to receive the user selection of the scan protocol. Specifically, receiving the user selection may include, at 830, the intelligent automated protocoling system automatically selecting one of the at least one protocol recommendations. For example, the intelligent automated protocoling system may select the protocol recommendation from the at least one protocol recommendations having the highest confidence weight. Then, at 835, receiving the user selection may further include determining whether a user confirmation of the automatically selected protocol recommendation is received. In some embodiments, if the level of confidence of a given protocol recommendation is below a threshold level of confidence, then confirmation may be sought from a medical professional with a relatively high experience level (e.g., a radiologist). In some embodiments, automatic selection from the at least one protocol recommendations may be actuatable by the user of the medical imaging system, such that, in individual instances, automatic selection may not be utilized. In some embodiments, a user modification to the automatically selected protocol recommendation may then be received following the user confirmation. In additional or alternative embodiments, a selection count corresponding to a user-modified scan protocol may be reset so as to account for the user modification.

If the confirmation of the automatically selected protocol recommendation is not received, receiving the user selection may include, at 820, receiving the manual user selection of the scan protocol from the user of the medical imaging system. In some embodiments, the manual user selection may include a user selection of one of the at least one protocol recommendations displayed to the user. In additional or alternative embodiments, the manual user selection may include a user selection of a scan protocol not corresponding to any of the at least one protocol recommendations displayed to the user.

If the confirmation of the automatically selected protocol recommendation is received (e.g., at 835), or if the manual user selection is received (e.g., at 820), then method 800 may proceed to 840 to increment a selection count (e.g., by one) of a selected scan protocol. As such, the selected scan protocol may correspond to the confirmed, automatically selected protocol recommendation or to a manually selected scan protocol. Then, at 845, method 800 may include updating the mapping database (e.g., the local procedure-to-protocol mapping library) based on the selected scan protocol and the incremented selection count.

At 850, method 800 may include executing a scan session based on the selected scan protocol. Specifically, the intelligent automated protocoling system may translate the selected scan protocol to a scan protocol executable, which may then be executed by the medical imaging system as the scan session.

An image may ultimately be generated based on the scan session. As such, at 855, method 800 may include displaying the generated image at the display device such that the user may view the generated image. Then, at 860, method 800 may include receiving a diagnosis of a medical issue based on the generated image. In this way, displaying the image generated by the scan session executed based on the selected scan protocol may allow the user to make more informed and consistent diagnoses. That is, since the intelligent automated protocoling system may account for prior protocol selections, a consistency of protocol recommendation and automatic selection therefrom may be incrementally improved over time, which may concomitantly improve a consistency of diagnoses by the user. Method 800 may then end.

In this way, an intelligent automated protocoling system for a medical imaging system is provided for recommending and selecting a scan protocol based on local identifiers, where the local identifiers may be alphanumeric codes specific to a medical facility corresponding to the medical imaging system. Specifically, the intelligent automated protocoling system may map the local identifiers to modality work list (MWL) entries to provide a "lingua franca" for generating protocol recommendations. A technical effect of leveraging the MWL entries to generate protocol recommendations is that a consistency of the protocol recommendations may be maintained regardless of the medical facility with which the local identifiers are associated, thereby improving patient experience and health outcomes. Further, for each scan session, the intelligent automated protocoling system may immediately update a procedure-to-protocol mapping library based on input from a medical professional. A technical effect of updating the procedure-to-protocol mapping library based on such incremental feedback from one or more medical professionals is that the intelligent automated protocoling system may alter protocol recommendations over time for a given medical situation based on accumulated medical expertise gleaned from the incremental feedback.

In one embodiment, a method comprises receiving, from a hospital-specific user interface, a standard procedure ID, determining a medical imaging procedure based on the standard procedure ID, and, responsive to having previously received the standard procedure ID, generating one or more protocol recommendations based at least on the determined medical imaging procedure, and performing the determined medical imaging procedure based on at least one of the one or more protocol recommendations. In a first example of the method, receiving the standard procedure ID comprises receiving, at the hospital-specific user interface, a modality worklist (MWL) entry, and determining the standard procedure ID based on the MWL entry. In a second example of the method, optionally including the first example of the method, generating the one or more protocol recommendations is further based on additional information from the MWL entry. In a third example of the method, optionally including one or more of the first and second examples of the method, the method further comprises displaying, at the hospital-specific user interface, the one or more protocol recommendations, and receiving, from the hospital-specific user interface, a selection of the at least one of the one or more protocol recommendations. In a fourth example of the method, optionally including one or more of the first through third examples of the method, the method further comprises, responsive to not having previously received the standard procedure ID, displaying, at the hospital-specific user interface, an indication that no protocol recommendations were generated. In a fifth example of the method, optionally including one or more of the first through fourth examples of the method, the method further comprises receiving, from the hospital-specific user interface, a manual protocol selection, and performing the determined medical imaging procedure based on the manual protocol selection. In a sixth example of the method, optionally including one or more of the first through fifth examples of the method, performing the determined medical imaging procedure based on the one of the one or more protocol recommendations comprises initiating an imaging scan session according to the at least one of the one or more protocol recommendations, and diagnosing a patient based on the imaging scan session.

In another embodiment, a medical imaging system comprises an intelligent automated protocoling system configured to map DICOM tags to imaging protocols, a mapping database comprising a plurality of imaging protocols, a display device, and a processor communicably coupled to each of the intelligent automated protocoling system, the mapping database, and the display device, the processor configured with instructions in non-transitory memory that when executed cause the processor to receive, from a user, a modality worklist (MWL) entry, the MWL entry corresponding to one or more DICOM tags, automatically generate one or more protocol recommendations, and, responsive to the one or more protocol recommendations corresponding to at least one of the plurality of imaging protocols, display to the user, via the display device, the one or more protocol recommendations, and, responsive to receiving a selection of a first imaging protocol from the one or more protocol recommendations, initiating a medical imaging scan according to the first imaging protocol. In a first example of the medical imaging system, the processor is further configured to correlate the MWL entry to a local procedure ID, and select, from the mapping database, the at least one of the plurality of imaging protocols based on the local procedure ID. In a second example of the medical imaging system, optionally including the first example of the medical imaging system, the processor is further configured to, responsive to at least one second imaging protocol from the one or more protocol recommendations not corresponding to any of the plurality of imaging protocols, log an indication that the at least one second imaging protocol is not stored in the mapping database. In a third example of the medical imaging system, optionally including one or more of the first and second examples of the medical imaging system, the processor is further configured to map, via the intelligent automated protocoling system, the one or more DICOM tags to the at least one of the plurality of imaging protocols. In a fourth example of the medical imaging system, optionally including one or more of the first through third examples of the medical imaging system, receiving the selection of the first imaging protocol from the one or more protocol recommendations comprises automatically selecting the first imaging protocol from the one or more protocol recommendations, and receiving, from the user, confirmation of the automatically selected first imaging protocol. In a fifth example of the medical imaging system, optionally including one or more of the first through fourth examples of the medical imaging system, receiving the selection of the first imaging protocol from the one or more protocol recommendations comprises receiving, from the user, a manual selection of the first imaging protocol. In a sixth example of the medical imaging system, optionally including one or more of the first through fifth examples of the medical imaging system, the processor is further configured to, responsive to not receiving the selection of the first imaging protocol from the one or more protocol recommendations, receive, from the user, a manual selection of a second imaging protocol, the second imaging protocol not included in the one or more protocol recommendations, and initiating the medical imaging scan according to the second imaging protocol. In a seventh example of the medical imaging system, optionally including one or more of the first through sixth examples of the medical imaging system, the processor is further configured to update the mapping database with the second imaging protocol.

In yet another embodiment, a method comprises receiving a local imaging procedure, generating one or more protocol recommendations based on the local imaging procedure, retrieving, from a database, a selection count for each of the one or more protocol recommendations, and, responsive to a selection count for at least one of the one or more protocol recommendations being greater than a selection count threshold, displaying, to a user, the at least one of the one or more protocol recommendations, receiving, from the user, a selected protocol recommendation from the at least one of the one or more protocol recommendations, increasing a selection count of the selected protocol recommendation, updating the database with the increased selection count for the selected protocol recommendation, and imaging a patient according to the selected protocol recommendation. In a first example of the method, the method further comprises, responsive to the user modifying the selected protocol recommendation prior to imaging, increasing a selection count for the modified protocol recommendation, updating the database with the increased selection count for the modified protocol recommendation, and imaging the patient according to the modified protocol recommendation. In a second example of the method, optionally including the first example of the method, the method further comprises, responsive to no selection count of the one or more protocol recommendations being greater than the selection count threshold, receiving, from the user, a manually-entered protocol, increasing a selection count for the manually-entered protocol, updating the database with the increased selection count for the manually-entered protocol, and imaging the patient according to the manually-entered protocol. In a third example of the method, optionally including one or more of the first and second examples of the method, the method further comprises retrieving, from the database, a confidence weight for each of the one or more protocol recommendations. In a fourth example of the method, optionally including one or more of the first through third examples of the method, a confidence weight for each of the at least one of the one or more protocol recommendations is greater than a threshold confidence weight.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method executable via instructions stored in memory of an intelligent automated protocoling system, comprising:
   receiving an indication of a local imaging procedure to be performed on a patient;
   retrieving, from a mapped Digital Imaging and Communications in Medicine (DICOM) tags database stored in memory of the intelligent automated protocoling system, one or more DICOM tags associated with the local imaging procedure;
   generating one or more protocol recommendations based on a local procedure-to-protocol mapping stored in memory of the intelligent automated protocoling system, the local procedure-to-protocol mapping configured to match the one or more DICOM tags associated with the local imaging procedure to the one or more protocol recommendations based on the one or more protocol recommendations each having one or more DICOM tags that match one or more of the one or more DICOM tags associated with the local imaging procedure;
   retrieving, from the local procedure-to-protocol mapping, a respective selection count for each of the one or more protocol recommendations, each respective selection count saved in memory of the intelligent automated protocoling system as part of the local procedure-to-protocol mapping; and responsive to the respective selection count for at least one of the one or more protocol recommendations being greater than a selection count threshold:

displaying, to a user, the at least one of the one or more protocol recommendations, receiving, from the user, a selected protocol recommendation from the at least one of the one or more protocol recommendations, increasing the respective selection count of the selected protocol recommendation, updating the local procedure-to-protocol mapping with the increased selection count for the selected protocol recommendation, retrieving a scan protocol corresponding to the selected protocol recommendation from a master protocol library, and executing, with a medical imaging system operably coupled to the intelligent automated protocoling system, the scan protocol in order to image the patient according to the scan protocol recommendation.

2. The method of claim 1, further comprising, responsive to the user modifying the selected protocol recommendation prior to imaging:

increasing the respective selection count for the modified protocol recommendation, updating the database with the increased selection count for the modified protocol recommendation, and imaging the patient according to the modified protocol recommendation.

3. The method of claim 1, further comprising, responsive to no selection count of the one or more protocol recommendations being greater than the selection count threshold, receiving, from the user, a manually-entered protocol, increasing a selection count for the manually-entered protocol, updating the database with the increased selection count for the manually-entered protocol, and imaging the patient according to the manually-entered protocol.

4. The method of claim 1, further comprising retrieving, from the database, a confidence weight for each of the one or more protocol recommendations, wherein a confidence weight for each of the at least one of the one or more protocol recommendations is greater than a threshold confidence weight.

5. The method of claim 1, wherein receiving the indication of the local imaging procedure to be performed on the patient comprises receiving a modality worklist (MWL) entry selection and determining the local imaging procedure based on the MWL entry via a MWL processing module of the intelligent automated protocoling system.

\* \* \* \* \*